United States Patent
Wix

(10) Patent No.: US 6,736,139 B1
(45) Date of Patent: May 18, 2004

(54) VENTILATION MASK ASSIST DEVICE

(76) Inventor: Mark Wix, 5226 E. Turquoise, Paradise Valley, AZ (US) 85253

(*) Notice: Subject to any disclaimer, the term of this patent is extended or adjusted under 35 U.S.C. 154(b) by 0 days.

(21) Appl. No.: 10/370,802

(22) Filed: Feb. 20, 2003

(51) Int. Cl.$^7$ .............................. A62B 18/02
(52) U.S. Cl. ..................... 128/206.21; 128/206.29
(58) Field of Search .................... 128/848, 859, 128/860, 861, 863, 200.26, 200.27, 201.15, 201.23, 201.26, 201.27, 206.12, 206.18, 206.21, 206.23, 206.24, 206.26, 206.28, 206.29, 207.13, DIG. 26

(56) References Cited

U.S. PATENT DOCUMENTS

| | | | |
|---|---|---|---|
| 1,139,850 A | | 5/1915 | Conkle |
| 3,013,556 A | | 12/1961 | Galleher |
| 3,303,845 A | * | 2/1967 | Detmer, III ............ 128/202.28 |
| 3,330,274 A | | 7/1967 | Bennett |
| 3,774,616 A | * | 11/1973 | White et al. ............ 128/200.26 |
| 4,258,710 A | | 3/1981 | Reber |
| 4,270,531 A | | 6/1981 | Blachly et al. |
| 4,274,406 A | | 6/1981 | Bartholomew |
| 4,437,462 A | | 3/1984 | Piljay et al. |
| 4,706,683 A | * | 11/1987 | Chilton et al. ............ 600/431 |
| 5,074,297 A | | 12/1991 | Venegas |
| 5,174,284 A | * | 12/1992 | Jackson ................ 128/200.26 |
| 5,431,158 A | | 7/1995 | Tirotta |
| 5,533,523 A | * | 7/1996 | Bass et al. ................. 128/859 |
| 5,542,128 A | | 8/1996 | Lomas |
| 5,603,317 A | | 2/1997 | Farmer |
| 5,660,174 A | | 8/1997 | Jacobelli |
| 5,662,101 A | | 9/1997 | Ogden et al. |
| 6,039,044 A | | 3/2000 | Sullivan |
| 6,123,071 A | | 9/2000 | Berthon-Jones et al. |
| 6,256,524 B1 | * | 7/2001 | Walker et al. .............. 600/340 |
| 6,371,112 B1 | * | 4/2002 | Bibi ...................... 128/204.18 |
| 6,374,826 B1 | | 4/2002 | Gunaratnam et al. |
| D464,427 S | | 10/2002 | Smart |
| 6,533,761 B2 | * | 3/2003 | Bertoch et al. ............. 604/174 |
| 6,606,991 B2 | * | 8/2003 | Chou .................... 128/200.26 |
| 2001/0015206 A1 | | 8/2001 | Arndt |
| 2002/0033175 A1 | * | 3/2002 | Bateman et al. ......... 128/201.18 |
| 2003/0183227 A1 | * | 10/2003 | Klemperer ............ 128/201.26 |

* cited by examiner

Primary Examiner—Henry Bennett
Assistant Examiner—Teena Mitchell
(74) Attorney, Agent, or Firm—Frank J. McGue

(57) ABSTRACT

A ventilation mask assist device is provided for use in anesthesia of a patient with an obstruction to provide an airtight seal when using a ventilation face mask. The ventilation mask assist device has an outer flap, an inner flap and a perioral extension extending through and connecting the outer flap and the inner flap. The perioral extension extends through a mouth of the patient and provides gaseous communication between the interior of the mouth and the ventilator mask. The outer flap is shaped to extend over the obstruction to cover cheeks and a chin of the patient. The edge of the conventional face mask contacts the outer flap and provides an airtight seal therebetween. The inner flap is shaped to cover the buccal side of the cheeks.

16 Claims, 2 Drawing Sheets

VENTILATION MASK ASSIST DEVICE

TECHNICAL FIELD

This invention relates in general to masks for use in anesthesiology, and, more particularly, to a ventilation mask assist device for use with patients having facial characteristics preventing an airtight seal for patients.

BACKGROUND OF THE INVENTION

When a patient is subject to anesthesia, for example, during a surgical procedure, there is a period of time when respiration is taken over by the anesthesiologist. The ability to ventilate the patient properly for respiration requires an airtight seal with a ventilation face mask around the patient's mouth and nose. Currently, the ventilation face mask is a generally triangular shape to accommodate the nose and mouth of a typical patient. A soft, pliable edge is employed which, when pressed against a face, generally provides the airtight seal needed for proper ventilation.

However, a problem arises if the patient has a facial obstruction which interferes with an airtight seal. Such characteristics include, but are not limited to, facial hair such as a beard or a facial deformity.

There are a number of techniques to counter the problem. One solution is to provide a larger face mask to increase the surface area in contact with the face. However, this solution generally is ineffective with some obstructions such as thick beards. Oral airways and nasal trumpets can be employed to decrease air flow resistance into the patient, but such techniques do not solve the underlying problem of a lack of the airtight seal. A laryngeal mask airway is possible as it is designed to sit over the vocal cords well past any problem on the face. However, sometimes the laryngeal mask airway does not sit well over the larynx and thereby fails to provide the airtight seal with increased peak inspiratory pressures even when properly in place.

Another current technique is to push the oxygen flush valve on the anesthesia machine thereby refilling the anesthesia circuit bag and allowing a single quick but incomplete breath. This technique is normally used only until the patient is intubated or some other means of maintaining an airway is secured. If the airway is not secured promptly, the anesthesiologist is left with few options to overcome the problem of the lack of the airtight seal. Thus, there is a need for a device to provide an airtight seal to patients with obstructions.

Ventilation devices are known in the art.

U.S. Pat. No. 4,270,531 entitled "Oropharyngeal Airway and Bite Block Assembly and Method for Closed Pulmonary Ventilation" which issued on Jun. 2, 1981 to Blachly discloses a bite block device for use in combination with an oropharyngeal airway tube and a conventional mask to provide an airtight seal. However, this device does not address the problem of facial hair preventing an air tight seal between the conventional mask and the face.

None of the references cited disclose the present invention.

SUMMARY OF THE INVENTION

It is an object of this invention to provide a device for use with a conventional ventilator mask to provide an airtight seal for anesthesiological purposes for patients with obstructions.

Further objects and advantages of the invention will become apparent as the following description proceeds and the features of novelty which characterize this invention will be pointed out with particularity in the specification annexed hereto.

DESCRIPTION OF THE PREFERRED EMBODIMENT

Figure 1:
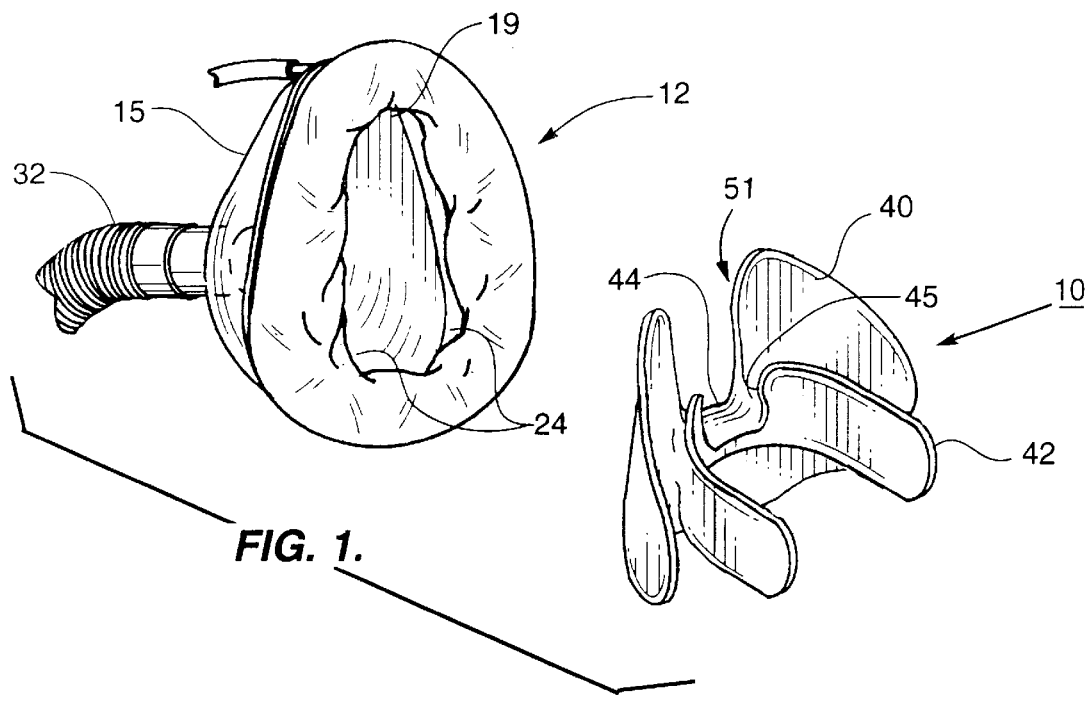
FIG. 1 is a perspective view of a ventilation mask assist device of the present invention aligned with a ventilation face mask.
Figure 2:
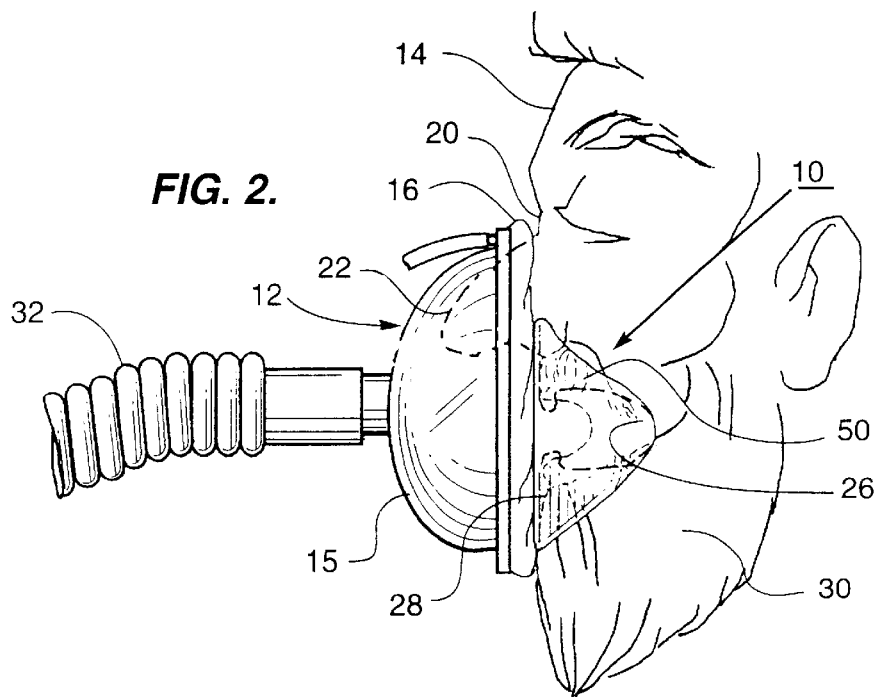
FIG. 2 is a side view showing the ventilation mask assist device of the present invention in use with a ventilation face mask.

The present invention as shown in FIGS. 1–5 is a ventilation mask assist device 10 used in connection with a ventilation face mask 12. As best shown in FIG. 2, ventilation face mask 12 is used during anesthesia of a patient 14 to assist in respiration of that patient. Ventilation face mask 12 generally comprises a soft, pliable plastic border 16 extending from a cover 15 connected to a tube 32 which outlines a rounded generally triangular opening.

In use, border 16 will have an upper vertex 19 of triangular opening placed over a bridge 20 of a nose 22 of patient 14. Border 16 extends downwardly and outwardly across cheeks 23 to two lower vertices 24 which are positioned on either side of a mouth 26 of patient 14 and then extends laterally across a chin 28 of patient 14. In general use, the soft pliable nature of border 16 creates an airtight seal between said border and the skin of patient 14. Thus, when air is forced via tube 32 into cover 15, said air will be forced into the airways of patient 14 to provide respiration therefor.

However, in the case of a patient 14 with an obstruction 30 such as a beard, obstruction 30 will prevent the airtight seal needed to force the air into patient 14.

To alleviate the problem, ventilation mask assist device 10 is inserted into mouth 26.

Figure 3:
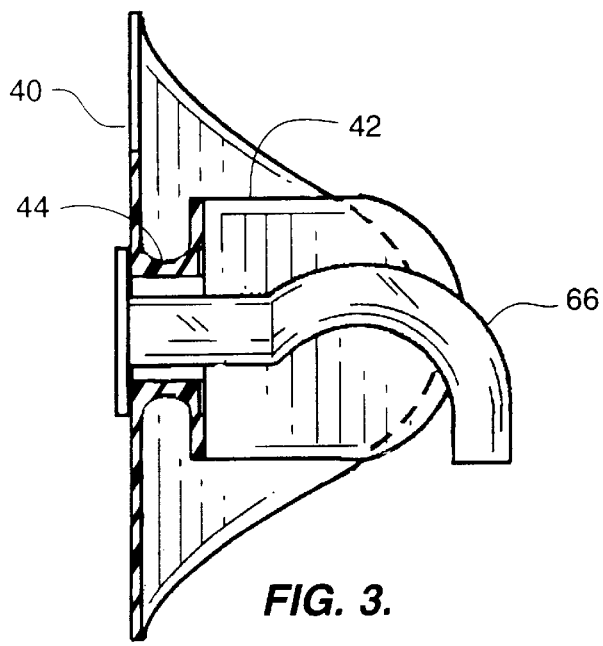
FIG. 3 is a cross sectional side view of an alternate embodiment of the ventilation mask assist device used in combination with an oral airway.

As best seen in FIGS. 1 and 3, device 10 comprises an outer flap 40, an inner flap 42 and a perioral extension 44 extending through and connecting both outer flap 40 and inner flap 42.

In use, perioral extension 44 forms a trench 45 extending through mouth 26 of patient 14 and provides gaseous communication between the interiors of mouth 26 and ventilation face mask 12. Inner flap 42 is contained within mouth 26 while outer flap 40 is on the face of patient 14.

Outer flap 40 is shaped to extend to cover beyond the portion of obstruction 30 which touches border 16. Outer flap 40 extends laterally from perioral extension 44 to cover cheeks 23 and downwardly to cover chin 28. Further, outer flap 40 curves towards perioral extension 44 to conform to the shape of the face. Thus, when border 16 is placed over patient 14, said border contacts outer flap 40 instead of obstruction 30 to provide the airtight seal needed to properly provide respiration to patient 14 despite obstruction 30.

Figure 4:
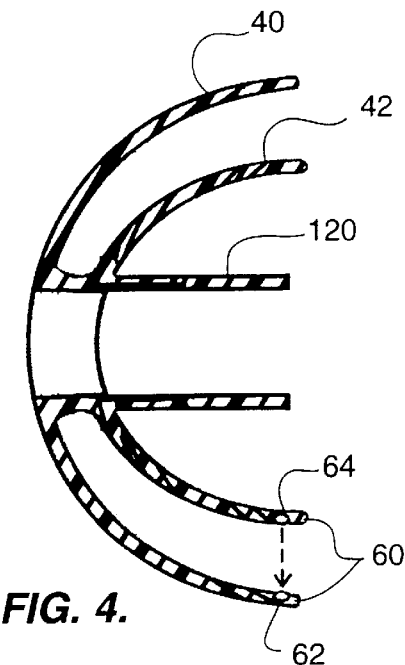
FIG. 4 is a cross sectional top view of another embodiment of the ventilation mask assist device of FIG. 1.
Figure 5:
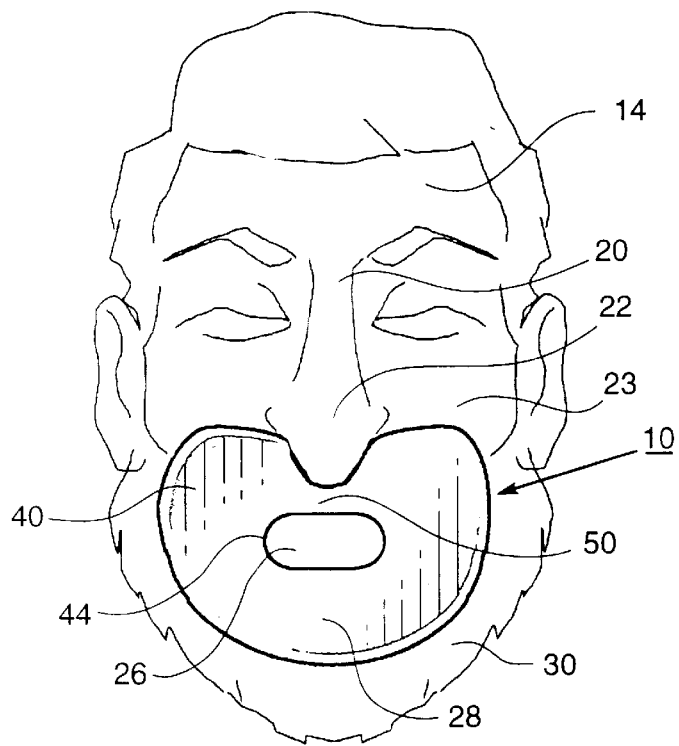
FIG. 5 is a front view of an alternate embodiment of the ventilation mask assist device of FIG. 3.

In the alternate embodiments of FIGS. 3–5, outer flap 40 extends over an upper lip 50 of patient 14. However, such coverage is generally not needed since border 16 extends over bridge 20 of nose 22, not said upper lip 50. Thus, the embodiments of FIGS. 1–2 showing a device 10 which defines a gap 51 in outer flap 40 which is an extension of trench 45 of perioral extension 44. Gap 51 corresponds to the position of upper lip 50. This most preferred embodiment also allows the anesthesiologist to retract the mouth 26 to assist in keeping mouth 26 open during intubation attempts.

Inner flap 42 is shaped to cover the buccal side of the teeth, i.e., between the teeth and the cheek of patient 14. Inner flap is generally oval shaped and extends away from perioral extension 44 to conform to the interior curvature of mouth 26. The long axis of the oval shaped inner flap extends along the gum line when device 10 is properly placed within mouth 26 of patient 14.

Another alternate embodiments of the invention are shown in FIGS. 3 and 4. In FIG. 4, an oximeter 60 comprising a sensor 62 and a light source 64 are provided. As is well known in the art, measuring the amount of light received by sensor 62 from light source 64 is used to determine the amount of oxygen carried within the blood of patient 14, a critical measurement for anesthesiologists to determine the efficacy of the patient's respiratory function. While usually oximeters are used on fingertips or ear lobes, the present invention suggests use on the cheek of a patient.

In addition, FIG. 3 shows the present invention in use in conjunction with an oral airway 66 which can be employed if desired.

Device 10 is preferably manufactured from latex-free plastics, well known in the art, to avoid allergic reactions from patient 14 and most preferably is made from a clear material allowing the anesthesiologist a clear view of the mouth and throat of patient 14. In still another embodiment shown in FIG. 4, perioral extension 44 is manufactured with a bite block 120 extending rearwardly from inner flap 42. Bite block 120 is positioned to prevent a patient's teeth from closing.

Although only certain embodiments have been illustrated and described, it will be apparent to those skilled in the art that various changes and modifications may be made therein without departing from the spirit of the invention.

What is claimed is:

1. A ventilation mask assist device for use in anesthesia during a positive pressure ventilation of a patient with a facial obstruction, the ventilation mask assist device being used in combination with a ventilation face mask, the ventilation mask assist device comprising;
    an outer flap which covers a chin and cheeks of a patient,
    a perioral extension of the outer flap that continues into an oral cavity of the patient, and
    an inner flap that extends from the perioral extension which extends along an inner surface of lips and the cheeks of a patient,
    whereby the ventilation mask assist device when used in combination with the ventilation face mask provides an airtight seal during the positive pressure ventilation.

2. The ventilation mask assist device of claim 1 wherein the outer flap curves rearwardly and conforms to the shape of the face.

3. The ventilation mask assist device of claim 1 wherein the inner flap extends along an interior surface of the cheeks.

4. The ventilation mask assist device of claim 3 wherein the inner flap extends along the gum line.

5. The ventilation mask assist device of claim 1 wherein the outer flap defines a gap which corresponds to and extends laterally along an upper lip of the patient.

6. The ventilation mask assist device of claim 1 further comprising an oximeter having a sensor and a light source, one of the sensor and the light source being placed on the inner flap and the other of the sensor and the light source being placed on a corresponding position on the outer flap, the sensor measuring the amount of light received from the light source through the cheek of the patient, the oximeter calculating the amount of oxygen in the patient's blood thereby.

7. The ventilation mask assist device of claim 1 adapted for use in combination with an oral airway.

8. The ventilation mask assist device of claim 1 manufactured from latex-free plastics.

9. The ventilation mask assist device of claim 1 manufactured from a clear plastic material.

10. The ventilation mask assist device of claim 1 wherein the perioral extension is manufactured from a hard plastic material to form a bite block.

11. A ventilation mask assist device for use in anesthesia during a positive pressure ventilation of a patient with a facial obstruction, the ventilation mask assist device being used in combination with a ventilation face mask, the ventilation mask assist device comprising;
    an outer flap which outer flap curves rearwardly and conforms to the shape of the face to cover a chin and cheeks of a patient, the outer flap defining a gap which corresponds to and extends laterally along an upper lip of the patient,
    a perioral extension of the outer flap that continues into an oral cavity of the patient, and
    an inner flap that extends from the perioral extension which extends along an interior surface of the cheeks along the gum line of a patient,
    whereby the ventilation mask assist device when used in combination with the ventilation face mask provides an airtight seal during the positive pressure ventilation.

12. The ventilation mask assist device of claim 11 further comprising an oximeter having a sensor and a light source, one of the sensor and the light source being placed on the inner flap and the other of the sensor and the light source being placed on a corresponding position on the outer flap, the sensor measuring the amount of light received from the light source through the cheek of the patient, the oximeter calculating the amount of oxygen in the patient's blood thereby.

13. The ventilation mask assist device of claim 11 adapted for use in combination with an oral airway.

14. The ventilation mask assist device of claim 11 manufactured from latex-free plastics.

15. The ventilation mask assist device of claim 11 manufactured from a clear plastic material.

16. The ventilation mask assist device of claim 11 wherein the perioral extension is manufactured from a hard plastic material to form a bite block.

* * * * *